US011761924B2

(12) United States Patent
Suzuki et al.

(10) Patent No.: US 11,761,924 B2
(45) Date of Patent: Sep. 19, 2023

(54) SENSOR ELEMENT, GAS SENSOR, AND GAS SENSOR UNIT

(71) Applicant: NGK SPARK PLUG CO., LTD., Nagoya (JP)

(72) Inventors: Yosuke Suzuki, Nagoya (JP); Takumi Yamada, Nagoya (JP); Hitoshi Furuta, Nagoya (JP); Kentaro Kamada, Nagoya (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 106 days.

(21) Appl. No.: 17/023,078

(22) Filed: Sep. 16, 2020

(65) Prior Publication Data
US 2021/0088471 A1 Mar. 25, 2021

(30) Foreign Application Priority Data

Sep. 20, 2019 (JP) ................................ 2019-171199
Jul. 23, 2020 (JP) ................................ 2020-125870

(51) Int. Cl.
*G01N 27/41* (2006.01)
*G01N 33/00* (2006.01)
*G01N 27/406* (2006.01)
*G01N 27/407* (2006.01)
*G01N 1/24* (2006.01)

(52) U.S. Cl.
CPC ............... *G01N 27/41* (2013.01); *G01N 1/24* (2013.01); *G01N 27/4065* (2013.01); *G01N 27/4071* (2013.01); *G01N 27/4075* (2013.01); *G01N 33/0037* (2013.01)

(58) Field of Classification Search
CPC ...... G01N 27/41; G01N 1/24; G01N 27/4065; G01N 27/4071; G01N 27/4075; G01N 33/0037; G01N 27/417; G01N 27/4074; G01N 27/409; G01N 27/419; Y02A 50/20
See application file for complete search history.

(56) References Cited

U.S. PATENT DOCUMENTS

| 7,445,700 B2 * | 11/2008 | Kato | ................... G01N 27/4072 73/23.31 |
| 2015/0013431 A1 * | 1/2015 | Kakimoto | ............ G01N 27/419 73/23.31 |
| 2015/0293051 A1 * | 10/2015 | Kajiyama | .......... G01N 27/4075 204/424 |
| 2018/0202965 A1 * | 7/2018 | Nakatou | ............ G01N 27/4075 |

FOREIGN PATENT DOCUMENTS

| EP | 928965 A2 * | 7/1999 | ......... G01N 27/4074 |
| JP | 6382162 B2 | 8/2018 | |

\* cited by examiner

*Primary Examiner* — Joshua L Allen
*Assistant Examiner* — Shizhi Qian
(74) *Attorney, Agent, or Firm* — Sughrue Mion, PLLC

(57) ABSTRACT

A sensor element (100) including a measurement chamber (89); a pump cell (83) including a solid electrolyte body (69), an inner electrode (101), and an outer electrode (99); and a reference cell (85). At least one electrode contains a noble metal and a component of the solid electrolyte body. In a cross section, the at least one electrode has a noble metal region (205), a solid electrolyte body region (203), and a coexistence region (207) in which the noble metal and the component of the solid electrolyte body coexist. Further, in the cross section, an area ratio SR of the coexistence region is not less than 15.5% and is less than 30%.

6 Claims, 6 Drawing Sheets

SENSOR ELEMENT, GAS SENSOR, AND GAS SENSOR UNIT

BACKGROUND OF THE INVENTION

1. Field of the Invention

The present invention relates to a sensor element, a gas sensor, and a gas sensor unit.

2. Description of the Related Art

With tightening regulation of exhaust gas discharged from an internal combustion engine of an automobile or the like, there is a need to reduce the amount of nitrogen oxides (NOx) contained in the exhaust gas. In view of the above, in recent years, development of an NOx sensor capable of directly measuring the concentration of NOx contained in exhaust gas has progressed. The NOx sensor includes an NOx sensor element having a pump cell and an NOx concentration detection cell each having a pair of electrodes formed on the surface of an oxygen-ion-conductive solid electrolyte body formed of, for example, zirconia.

In the NOx sensor, the pump cell pumps out oxygen from and into a measurement chamber which communicates with a space where a gas under measurement containing NOx is present. At that time, the pump cell is controlled such that the oxygen within the measurement chamber has a predetermined concentration. Furthermore, the NOx concentration of the gas under measurement whose oxygen concentration has been controlled (adjusted) is detected by the detection cell.

In the NOx sensor having the above-described structure, by providing electrodes alone on each solid electrolyte body, the electrodes of the NOx sensor element (detection element) cannot be activated to a sufficient degree. Consequently, the NOx sensor element fails to have satisfactory sensor characteristics.

In view of the foregoing, a technique has been proposed of applying a voltage between the pair of electrodes of the pump cell for aging treatment, thereby enhancing oxygen decomposition activity (see Patent Document 1). This technique shows that, when the ratio of a coexistence region which contains a noble metal contained in an electrode and a component of a solid electrolyte body is set to 30% or greater in a cross section of the electrode along the thickness direction thereof, the oxygen decomposition activity of the electrode is enhanced.

[Patent Document 1] Japanese Patent No. 6382162

Problems to be Solved by the Invention

However, since the coexistence region has poor joining performance, when the coexistence region of an electrode is excessively large, a problem of easy separation of the electrode from the solid electrolyte body arises. Also, in the case where the current flowing through the pump cell is feedback-controlled such that the potential of a reference cell becomes constant, the difference in response between the reference cell electrodes and the pump cell electrodes containing coexistence regions increases, so that oscillation may occur.

Meanwhile, when the coexistence region of the electrode is excessively small, the internal resistance of the electrode increases at low temperatures. In such a case, the voltage (Vp1) of the pump cell increases and causes problems such as decomposition of a to-be-measured component in exhaust gas.

SUMMARY OF THE INVENTION

The present invention has been accomplished in view of the above circumstances, and an object thereof is to provide a sensor element, a gas sensor, and a gas sensor unit in which the oxygen decomposition activity of an electrode (or electrodes) of a pump cell is enhanced and separation of the electrode (or the electrodes) from a solid electrolyte body is prevented.

The above object has been achieved by providing, in a first aspect of the invention, (1) a sensor element comprising: a measurement chamber; a pump cell for pumping out oxygen contained in a gas under measurement introduced into the measurement chamber and pumping oxygen into the measurement chamber, thereby adjusting oxygen concentration within the measurement chamber, the pump cell including a solid electrolyte body, an inner electrode formed on a surface of the solid electrolyte body that is exposed inside the measurement chamber, and an outer electrode formed on a surface of the solid electrolyte body that is located outside the measurement chamber; and a reference cell for generating a voltage corresponding to the oxygen concentration in the gas under measurement within the measurement chamber, wherein at least one electrode of the inner electrode and the outer electrode contains a noble metal and a component of the solid electrolyte body, and, when a cross section of the at least one electrode taken along a thickness direction thereof is observed, the one electrode has a noble metal region formed of the noble metal, a solid electrolyte body region formed of the component of the solid electrolyte body, and a coexistence region in which the noble metal and the component of the solid electrolyte body coexist, and wherein, in the cross section of the at least one electrode, an area ratio SR of the coexistence region represented by {an area of the coexistence region/(an area of the noble metal region+an area of the solid electrolyte body region+the area of the coexistence region)} is not less than 15.5% and is less than 30%.

According to the sensor element (1) above, the oxygen decomposition activity of the above-described at least one electrode of the pump cell can be enhanced, and since the area of the coexistence region which has poor joining performance is not excessively large, separation of the above-described one electrode from the solid electrolyte body can be prevented.

Also, in the case where the current flowing through the pump cell is feedback-controlled such that the potential of the reference cell becomes constant, the difference in response between the electrodes of the reference cell and the above-described at least one electrode containing the coexistence region does not increase excessively. As a result, oscillation can be prevented.

Furthermore, it is possible to prevent an increase in the internal resistance of the above-described at least one electrode, which increase would otherwise occur when the area of the coexistence region is excessively small, thereby preventing the occurrence of a problematic phenomenon in which the voltage (Vp1) of the pump cell increases and the gas component to be measured decomposes. Notably, the voltage Vp1 is a voltage (pump voltage) applied between the two electrodes of the pump cell so as to cause a flow of pump current (Ip1) in a positive direction or a negative direction between the two electrodes of the pump cell, for pumping oxygen into or out of the measurement chamber.

In a preferred embodiment (2), the at least one electrode includes at least the inner electrode, and the area ratio SR of the coexistence region in the cross section of the inner electrode is not less than 15.5% and is less than 30%.

In general, in the case of a gas sensor having an NOx detection cell, in most cases the oxygen concentration is adjusted by pumping oxygen out of the measurement chamber. Since the inner electrode of the pump cell of the sensor element includes the coexistence region having the above-described area ratio, the oxygen concentration can be adjusted particularly effectively.

In another preferred embodiment (3) of the sensor element (1) or (2) above, the area ratio SR of the coexistence region is not less than 16% and is not greater than 27%.

In yet another preferred embodiment (4), the sensor element of any of (1) to (3) above further comprises an NOx detection cell for measuring the concentration of nitrogen oxide in the gas under measurement having an adjusted oxygen concentration, In a second aspect (5), the invention provides a gas sensor comprising the sensor element of any of (1) to (4) above, and a metallic shell which holds the sensor element.

In a third aspect (6), the invention provides a gas sensor unit comprising the gas sensor (5) above and a gas sensor control section connected to the gas sensor, wherein the gas sensor control section is configured to feedback-control current flowing through the pump cell such that the reference cell has a constant potential.

Effects of the Invention

According to the present invention, the oxygen decomposition activity of an electrode (or electrodes) of a pump cell is/are enhanced and separation of the electrode (or the electrodes) from a solid electrolyte body is prevented.

DESCRIPTION OF REFERENCE NUMERALS

Figure 1:
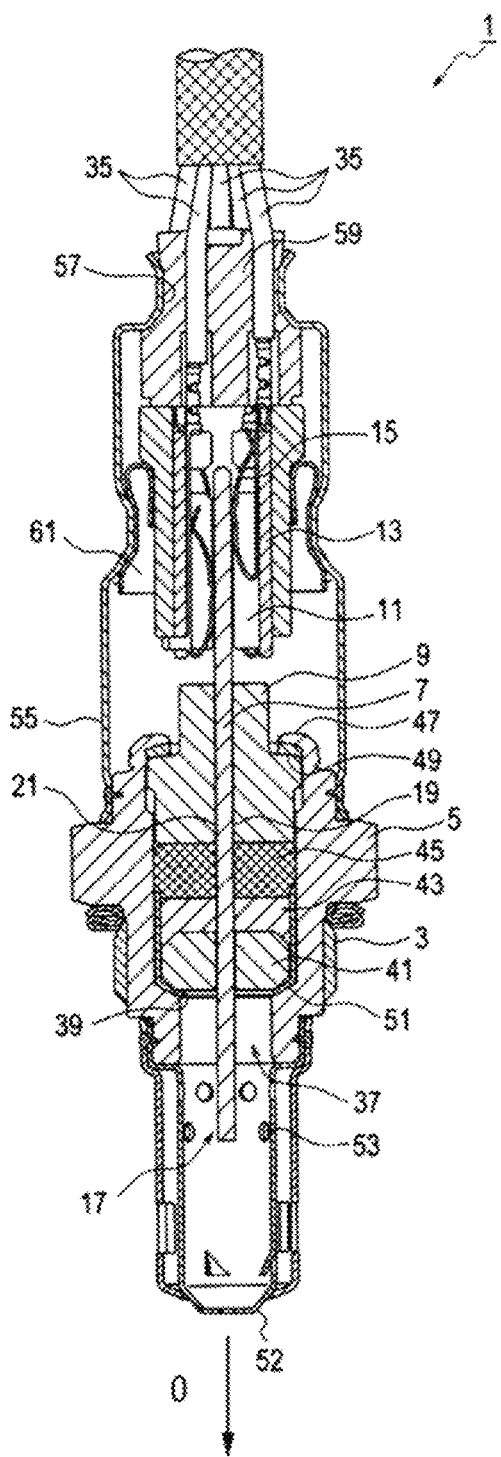
FIG. 1 is a cross-sectional view of an NOx sensor taken along an axial line thereof.

Reference numerals used to identify various features in the drawings include the following.

1 NOx sensor (gas sensor)
5 metallic shell
69 first solid electrolyte body (solid electrolyte body)
83 first pump cell (pump cell)
85 reference cell (reference cell)
87 second pump cell (NOx detection cell)
89 first measurement chamber (measurement chamber)
99 second electrode (outer electrode)
100 NOx sensor element (sensor element)
101 first electrode (inner electrode)
169 sensor control apparatus (gas sensor control section)
201 cross section
203 solid electrolyte body region
205 noble metal region
207 coexistence region
O axial line

DETAILED DESCRIPTION OF THE PREFERRED EMBODIMENTS

A gas sensor (NOx sensor) 1 according to an embodiment of the present invention will now be described with reference to the drawings. However, the present invention should not be construed as being limited thereto. FIG. 1 is a cross-sectional view of the NOx sensor 1 taken along an axial line O thereof. Notably, in the following description, the lower side in FIG. I will be referred to as the forward end side of the NOx sensor 1, and the upper side in FIG. I will be referred to as the rear end side of the NOx sensor 1.

As shown in FIG. 1, the NOx sensor 1 includes a metallic shell 5, a sensor element (an NOx sensor element) 7, a ceramic sleeve 9, an insulating separator 13, and six lead frames (metallic terminal members) 15. Notably, in FIG. 1, only some of the six lead frames 15 are illustrated.

The sensor element 7 is a plate-shaped laminated member extending in the direction of the axial line O. The sensor element 7 penetrates the metallic shell 5, and a forward end portion of the sensor element 7 is exposed to exhaust gas for measurement. The exhaust gas corresponds to the gas under measurement. The sensor element 7 has a detection section 17 formed at the forward end side thereof. The detection section 17 is covered with an unillustrated protection layer.

Figure 2:
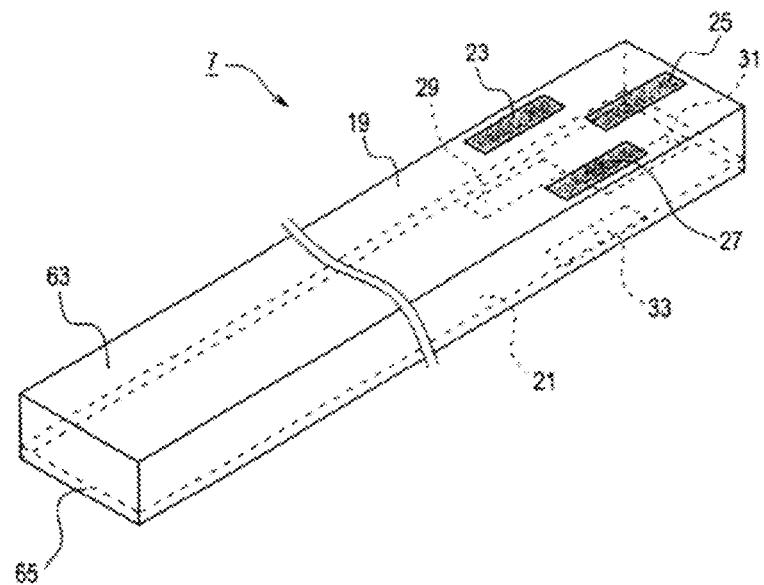
FIG. 2 is a perspective view of a sensor element with its portion in the direction of the axial line omitted.

As shown in FIG. 2, electrode pads 23, 25, 27, 29, 31 and 33 are formed at the rear end side of the sensor element 7. The electrode pads 23, 25, and 27 are formed on a first plate face 19 of the sensor element 7, which face is one of opposite outer surfaces of the sensor element 7. The electrode pads 29, 31, and 33 are formed on a second plate face 21 of the sensor element 7, which face is the other of the opposite outer surfaces of the sensor element 7 and is located opposite the first plate face 19.

The ceramic sleeve 9 has a tubular shape and surrounds the circumference of the sensor element 7. The insulating separator 13 is formed of, for example, an insulating material (alumina) and has an element insertion hole 11 extending therethrough in the direction of the axial line O. The wall surface of the element insertion hole 11 surrounds at least partially the sensor element 7 and the lead frames 15.

The insulating separator 13 holds the lead frames 15 and the sensor element 7 within the element insertion hole 11 so that the lead frames 15 are electrically connected to the electrode pads 23 to 33, respectively, of the sensor element 7. Since the lead frames 15 are also electrically connected to lead wires 35 extending from the outside to the interior of the sensor, current paths are formed for currents flowing between the electrode pads 23 to 33 and an external device to which the lead wires 35 are connected.

The metallic shell 5 is a metal member formed of, for example, stainless steel and has an approximately tubular shape. The metallic shell 5 has a through hole 37 extending therethrough in the direction of the axial line O and a ledge portion 39 protruding radially inward the through hole 37. The metallic shell 5 has a screw portion 3 which is formed on the outer surface of the metallic shell 5 and is used for fixing to an exhaust pipe. The metallic shell 5 is configured to hold the sensor element 7 inserted through the through hole 37 so that the detection section 17 of the sensor element 7 is disposed on the forward end side and externally of the through hole 37, and the electrode pads 23 to 33 are located on the rear end side and externally of the through hole 37.

In the through hole 37, an annular ceramic holder 41, powder charged layers (talc rings) 43 and 45, and the above-described ceramic sleeve 9 are stacked in this order from the forward end side toward the rear end side so as to surround the circumference of the sensor element 7.

A crimp ring 49 is disposed between the ceramic sleeve 9 and a rear end portion 47 of the metallic shell 5. A metallic cup 51 is disposed between the ceramic holder 41 and the ledge portion 39 of the metallic shell 5. Notably, the rear end portion 47 of the metallic shell 5 is crimped so as to press the ceramic sleeve 9 toward the forward end side through the crimp ring 49.

A tubular protector 52 formed of, for example, stainless steel is disposed on the forward end side of the metallic shell 5 to cover the forward end portion of the sensor element 7. The protector 52 has gas passage holes 53 through which the exhaust gas can flow. The protector 52 has a double protector structure composed of an inner protector and an outer protector.

An outer casing 55 formed of, for example, stainless steel is fixed to a rear end portion of the metallic shell 5. A rear-end-side opening 57 of the outer casing 55 is closed by a grommet 59 formed of, for example, a fluororubber.

Notably, the insulating separator 13 is held inside the outer casing 55 in a state in which the rear end of the insulating separator 13 is in contact with the grommet 59. The insulating separator 13 is held by a holding member 61. The holding member 61 is fixed to the inner side of the outer casing 55 by means of crimping.

Figure 3:
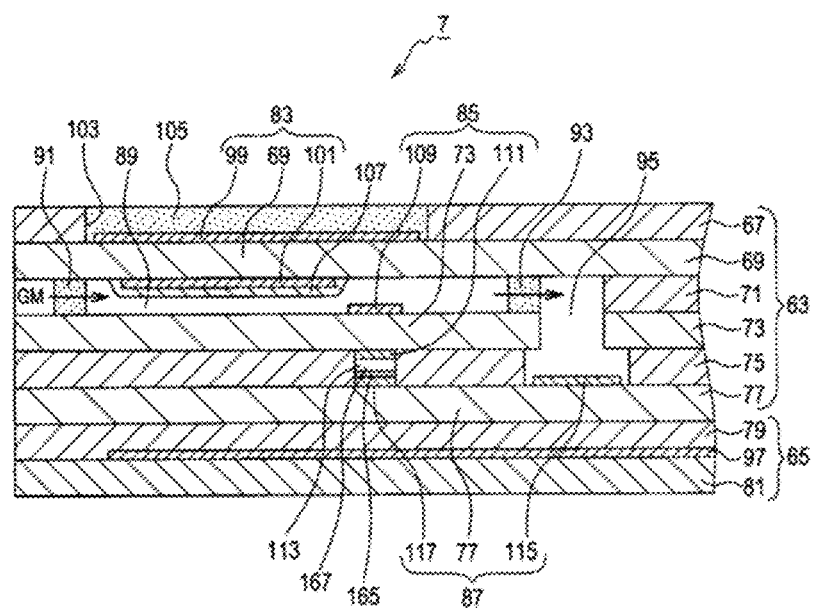
FIG. 3 is an explanatory view obtained by cutting a forward end portion of the sensor element in its thickness direction and showing, on an enlarged scale, the internal structure of the forward end portion.

Next, the structure of the sensor element 7 will be described with reference to FIGS. 2 and 3. FIG. 2 is a perspective view of the sensor element 7 with its portion in the direction of the axial line O omitted. FIG. 3 is an explanatory view obtained by cutting a forward end portion of the sensor element 7 in its thickness direction and showing, on an enlarged scale, the internal structure of the forward end portion.

As shown in FIG. 2, the sensor element 7 has the shape of a plate having a rectangular axial cross section and has a structure in which an element section 63 and a heater 65 are stacked together. Each of the element section 63 and the heater 65 is formed into the shape of a plate extending in the direction of the axial line O.

As shown in FIG. 3, the sensor element 7 includes an insulating layer 67, a first solid electrolyte body 69, an insulating layer 71, a second solid electrolyte body 73, an insulating layer 75, a third solid electrolyte body 77, and insulating layers 79 and 81, which are stacked in this order from the upper side in FIG. 3. Of these layers and bodies, the insulating layer 67, the first solid electrolyte body 69, the insulating layer 71, the second solid electrolyte body 73, the insulating layer 75, and the third solid electrolyte body 77 correspond to the element portion 63. The sensor element 7 includes a first pump cell 83, a reference cell 85, and a second pump cell 87.

A first measurement chamber 89 is formed between the first solid electrolyte body 69 and the second solid electrolyte body 73. In FIG. 3, the left end of the first measurement chamber 89 serves as an inlet. A first diffusion resistor section 91 is disposed at the inlet. Exhaust gas GM is introduced into the first measurement chamber 89 from the outside through the first diffusion resistor section 91. A second diffusion resistor section 93 is disposed at an end of the first measurement chamber 89 located opposite the inlet.

A second measurement chamber 95 is formed on the right side of the second diffusion resistor section 93. The second measurement chamber 95 communicates with the first measurement chamber 89 through the second diffusion resistor section 93. The second measurement chamber 95 is formed between the first solid electrolyte body 69 and the third solid electrolyte body 77. A portion of the second solid electrolyte body 73 corresponding to the second measurement chamber 95 is removed.

Each of the first to third solid electrolyte bodies 69, 73, and 77 contains, as a main component, zirconia having oxygen ion conductivity. Each of the insulating layers 67, 71, 75, 79, and 81 contains alumina as a main component. Each of the first and second diffusion resistor sections 91 and 93 is formed of a porous substance such as alumina. Notably, the main component of a ceramic layer means a component whose amount in the ceramic layer is 50 mass % or more.

A heating resistor element 97 is embedded between the insulating layers 79 and 81. The heating resistor element 97 extends in the lateral direction in FIG. 3. The heating resistor element 97 is formed of, for example, platinum. The insulating layers 79 and 81 and the heating resistor element 97 constitute the heater 65. The heater 65 heats the sensor element 7 to a predetermined activation temperature so as to increase the oxygen ion conductivity of the first to third solid electrolyte bodies 69, 73, and 77 for stable operation.

The first pump cell 83 includes the first solid electrolyte body 69, a first electrode 101, and a second electrode 99. The first electrode 101 and the second electrode 99 sandwich the first solid electrolyte body 69.

The first electrode 101 contains platinum, zirconia, coexistence regions described below, and pores. Zirconia corresponds to a ceramic component contained in the first solid electrolyte body 69. The second electrode 99 contains platinum as a main component.

The first electrode 101 faces the first measurement chamber 89. The surface of the first electrode 101 is covered with a porous layer 107 through which gases can pass. The second electrode 99 is exposed to an atmosphere outside the sensor element 7. The second electrode 99 is covered with a porous layer 105. The porous layer 105 is embedded in an opening 103 of the insulating layer 67. The porous layer 105 is formed of a porous material through which gases such as oxygen can pass. An example of the porous material is alumina.

The reference cell 85 includes the second solid electrolyte body 73, a third electrode 109 and a fourth electrode 111. The reference cell 85 generates a voltage corresponding to the concentration of oxygen contained in the gas under measurement within the first measurement chamber 89 (based on the atmosphere of the gas under measurement within the first measurement chamber 89). The third electrode 109 and the fourth electrode 111 sandwich the second solid electrolyte body 73. The third electrode 109 faces the first measurement chamber 89. The fourth electrode 111 faces a reference oxygen chamber 113, described below. Each of the third electrode 109 and the fourth electrode 111 contains platinum as a main component.

The reference oxygen chamber 113 is formed by removing a portion of the insulating layer 75. The reference oxygen chamber 113 is a space surrounded by the second solid electrolyte body 73, the third solid electrolyte body 77, and the insulating layer 75. In the reference oxygen chamber 113, the concentration of oxygen is maintained at a predetermined concentration.

The second pump cell 87 includes the third solid electrolyte body 77, a fifth electrode 115, and a sixth electrode 117. The fifth electrode 115 and the sixth electrode 117 are formed on one surface of the third solid electrolyte body 77. The fifth electrode 115 faces the second measurement chamber 95. The sixth electrode 117 faces the reference oxygen chamber 113. The fifth electrode 115 and the sixth electrode 117 are isolated from each other by the insulating layer 75. Each of the fifth electrode 115 and the sixth electrode 117 contains platinum as a main component. The sixth electrode 117 is covered with an insulating protection layer 165 formed of a porous material. A gap 167, which is a hollow space, is present in the reference oxygen chamber 113.

Notably, the first measurement chamber 89, the first solid electrolyte body 69, the first electrode 101, the second electrode 99, and the first pump cell 83 correspond to the "measurement chamber," the "solid electrolyte body," the "inner electrode," the "outer electrode," and the "pump cell," respectively, of the invention.

The reference cell 85 corresponds to the "reference cell" of the invention.

The second pump cell 87 corresponds to the "NOx detection cell" of the invention.

Also, a sensor control apparatus 169, described below, corresponds to the "gas sensor control section" of the invention.

Figure 4:
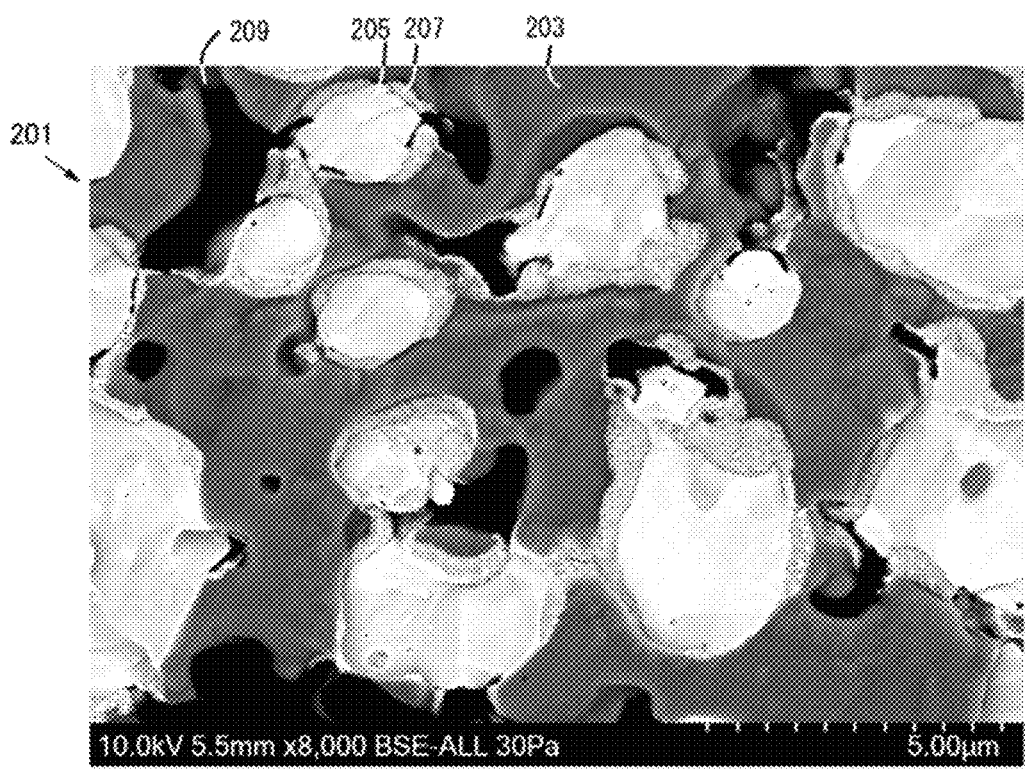
FIG. 4 is a representation of a backscattered electron image, obtained by an FE-SEM, of a cross section of a first electrode along the thickness direction thereof.

Next, the first electrode 101 will be described with reference to FIG. 4. FIG. 4 is a backscattered electron image, obtained by an FE-SEM (Field Emission Scanning Electron Microscope), of a cross section of the first electrode 101 along the thickness direction thereof.

As described above, when the cross section 201 is observed, the first electrode 101 contains noble metal regions 205 formed of platinum (noble metal), solid electrolyte body regions 203 formed of zirconia (the component of the solid electrolyte body), coexistence regions 207 in which the noble metal and the component of the solid electrolyte body coexist, and pores 209.

Notably, for example, an SEM image whose field of view has a size of 8.5 μm×12 μm can be used as the cross section 201.

A coexistence region area ratio SR represented by {the area of the coexistence regions 207/(the area of the noble metal regions 205+the area of the solid electrolyte body regions 203+the area of the coexistence regions 207)} is not less than 15.5% and is less than 30%.

As a result, the oxygen decomposition activity of the first electrode 101 of the first pump cell 83 can be enhanced. Also, since the area of the coexistence regions which are poor in joining performance is not excessively large, separation of the first electrode 101 from the first solid electrolyte body 69 can be prevented.

Also, in the case where the current flowing through the first pump cell 83 is feedback-controlled such that the potential of the reference cell 85 becomes constant, the difference in response between the detection electrode (the third electrode 109) and the first electrode 101 containing coexistence regions does not increase excessively. As a result, oscillation can be prevented.

Furthermore, it is possible to prevent an increase in the internal resistance of the first electrode 101, which increase would otherwise occur when the area of the coexistence regions is excessively small, thereby preventing the occurrence of a problematic phenomenon in which the voltage of the first pump cell 83 increases and the gas component to be measured is decomposed.

In the case where the area ratio SR of the coexistence regions 207 is less than 15.5%, the internal resistance of the first electrode 101 increases at low temperatures, and the voltage (Vp1) of the first pump cell 83 increases. Also, a specific gas which is a component of the gas under measurement to be measured is decomposed, whereby measurement accuracy is lowered.

Meanwhile, in the case where the area ratio SR of the coexistence regions 207 is 30% or greater, the first electrode 101 becomes more likely to separate from the first solid electrolyte body 69. This is because the coexistence regions 207 have poor joining performance at the time of firing of the electrode. Also, in the case where the current (Ip1) flowing through the first pump cell 83 is feedback-controlled such that the potential of the reference cell 85 becomes constant, the difference in response between the third electrode 109 and the first electrode 101 containing the coexistence regions 207 increases, which may cause oscillation.

Notably, the above-described oscillation (noise) of the current Ip1 stems from the feedback control of the first pump cell 83 performed based on the voltage of the reference cell 85.

The noble metal regions 205, the solid electrolyte body regions 203, the coexistence regions 207, and the pores 209 in the cross section 201 are determined as follows.

First, the cross section 201 is prepared by an FIB (Focused Ion Beam) process.

Subsequently, elemental analysis is performed for the cross section 201 by STEM/EDS (Scanning Transmission Electron Microscopy/Energy Dispersive X-ray Spectroscopy). Determination as to whether a given region is a coexistence region 207 or an alloy region is made by determining whether or not O (oxygen) is detected. In the case where O is detected, since the component of the solid electrolyte body is present in the form of $ZrO_2$, the given region is a coexistence region 207. In the case where O is not detected, since the component of the solid electrolyte body is present in the form of metal Zr, the subject region is an alloy region.

Also, the noble metal regions 205 and the solid electrolyte body regions 203 can be identified by the following EDS analysis.

Since the pores 209 hardly show reaction with incident electrons in the SEM image, the pores 209 appear black and can be distinguished from other regions.

The area of the coexistence regions 207 can be obtained through EDS analysis and analysis of the SEM image. Specifically, through the EDS analysis, the area A of regions containing the noble metal (Pt) (=the area of the noble metal regions 205+the area of the coexistence regions 207+the area of the alloy regions) and the area B of regions containing Zr (=the area of the solid electrolyte body regions 203+the area of the coexistence regions 207+the area of the alloy regions) is obtained.

A relation of (the area A+the area B)=(the area of the solid electrolyte body regions 203+the area of the noble metal regions 205+2×the area of the coexistence regions 207+2×the area of the alloy regions) is then obtained.

Next, the area C of the entire field of view, excluding the pores 209 (=the area of the solid electrolyte body regions 203+the area of the noble metal regions 205+the area of the coexistence regions 207+the area of the alloy regions) is obtained.

Since (the area A+the area B)−the area C=(the area of the coexistence regions 207+the area of the alloy regions), the area of the coexistence regions 207 is obtained by subtracting the area of the alloy regions (regions where O is not detected) from the result of (the area A+the area B)−the area C.

Namely, the coexistence regions 207 are regions where Zr is detected by EDS and exclude the regions where O is not detected, and their area ratio SR is 15.5%.

Figure 5:
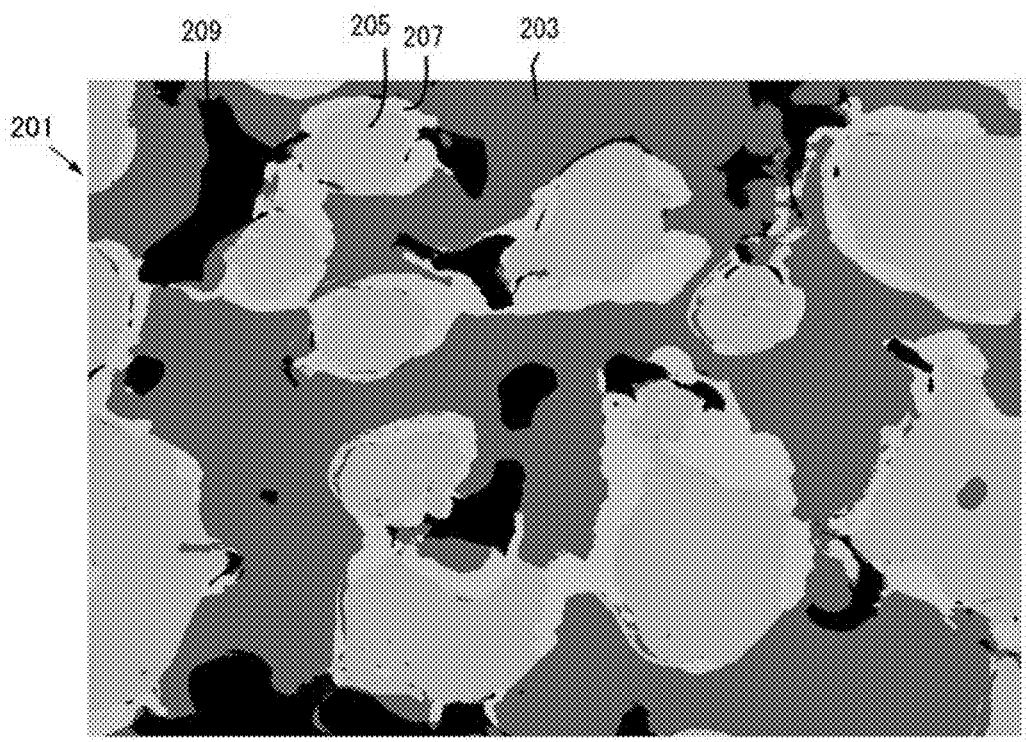
FIG. 5 is a representation of an image obtained from the image of FIG. 4 through composition (configuration) determination based on the magnitudes and variances of grayscale values of respective dots.

Notably, by increasing the contrasts of the respective regions by adjusting the contrast, etc. of the backscattered electron image of SEM shown in FIG. 5, it becomes possible to determine the noble metal regions 205, the solid electrolyte body regions 203, the coexistence regions 207, and the pores 209 without fail and to accurately obtain the areas A, B, and C.

For example, the SEM image in the BMP (Bitmap image file) format is converted to the CSV (Comma-Separated Values) format, and at that time, grayscale values are converted to numerical values in the color scale (RGB: 0 to 255). Subsequently, regions whose RGB numerical ranges fall within predetermined ranges are determined to be the same type of regions and are grouped. In this manner, the noble metal regions 205, the solid electrolyte body regions 203, the coexistence regions 207, and the pores 209 can be distinguished from one another.

Notably, although both the noble metal and the solid electrolyte body are present in each coexistence region 207, the coexistence region 207 can be distinguished, for example, by determining an area of 10×10 dots to be a coexistence region when the variances of the RGB numerical values of the noble metal and the solid electrolyte body in the area are equal to or greater than a predetermined value.

The coexistence region area ratio SR may be controlled to be not less than 15.5% and less than 30%, for example, by controlling conditions, such as temperature, application voltage, and application time, for the aging treatment of the first electrode 101. For example, when the aging treatment temperature, the application voltage, and the application time are increased, the coexistence region area ratio SR tends to increase.

For example, the conditions of the aging treatment are as follows.

The atmosphere of the first electrode: rich atmosphere

The temperature of the first electrode: not lower than 800° C. and lower than 950° C.

The voltage between the first electrode and the second electrode: 0.75 to 1.00 V The time of the aging treatment: 40 to 200 sec The rich atmosphere refers to an atmosphere in which the ratio of oxygen is smaller as compared with the theoretical air-fuel ratio ($\lambda=1$). The theoretical air-fuel ratio refers to the mixture ratio between air and fuel which allows ideal perfect combustion.

In the case where the aging treatment temperature is excessively high, since the internal resistance of the first solid electrolyte body 69 decreases, the current flowing through the first solid electrolyte body 69 during the aging treatment increases. Since the aging treatment is generally performed in an oxygen-deficient atmosphere, if the aging treatment temperature is excessively high, a blackening phenomenon in which the first pump cell works to pump out oxygen contained in the first solid electrolyte body 69 and thereby produce a current flow may occur. Accordingly, the aging temperature is preferably 1000° C. or lower.

It is sufficient that the coexistence region area ratio SR of at least one of the first electrode 101 and the second electrode 99 falls within the above-described range, and the coexistence region area ratios SR of both the electrodes 101 and 99 may fall within the above-described range. In particular, when at least the coexistence region area ratio SR of the first electrode 101 falls within the above-described range, a variation in the voltage of the pump cell due to, for example, a change in the flow velocity of the gas under measurement is suppressed, and measurement accuracy is increased.

For example, in the case of an NOx sensor, the effect obtained by specifying the area ratio SR of the first electrode 101 is high. This is because when exhaust gas is lean, a large amount of NOx is present and the first pump cell pumps out oxygen.

Also, even in the case of an oxygen sensor, the effect obtained by specifying the area ratio SR of the first electrode 101 is high when the exhaust gas is lean.

The means for heating the first electrode 101 and/or the second electrode 99 for the aging treatment may be the heater 65 or an external heater.

The first electrode and the second electrode may be aged simultaneously by alternatingly applying a positive voltage and a negative voltage between the first electrode and the second electrode, for example, by alternatingly applying a voltage between the first electrode and the second electrode. Alternatively, after the aging of one electrode is completed by applying a voltage of one polarity, the other electrode may be aged by applying a voltage of the opposite polarity.

Figure 6:
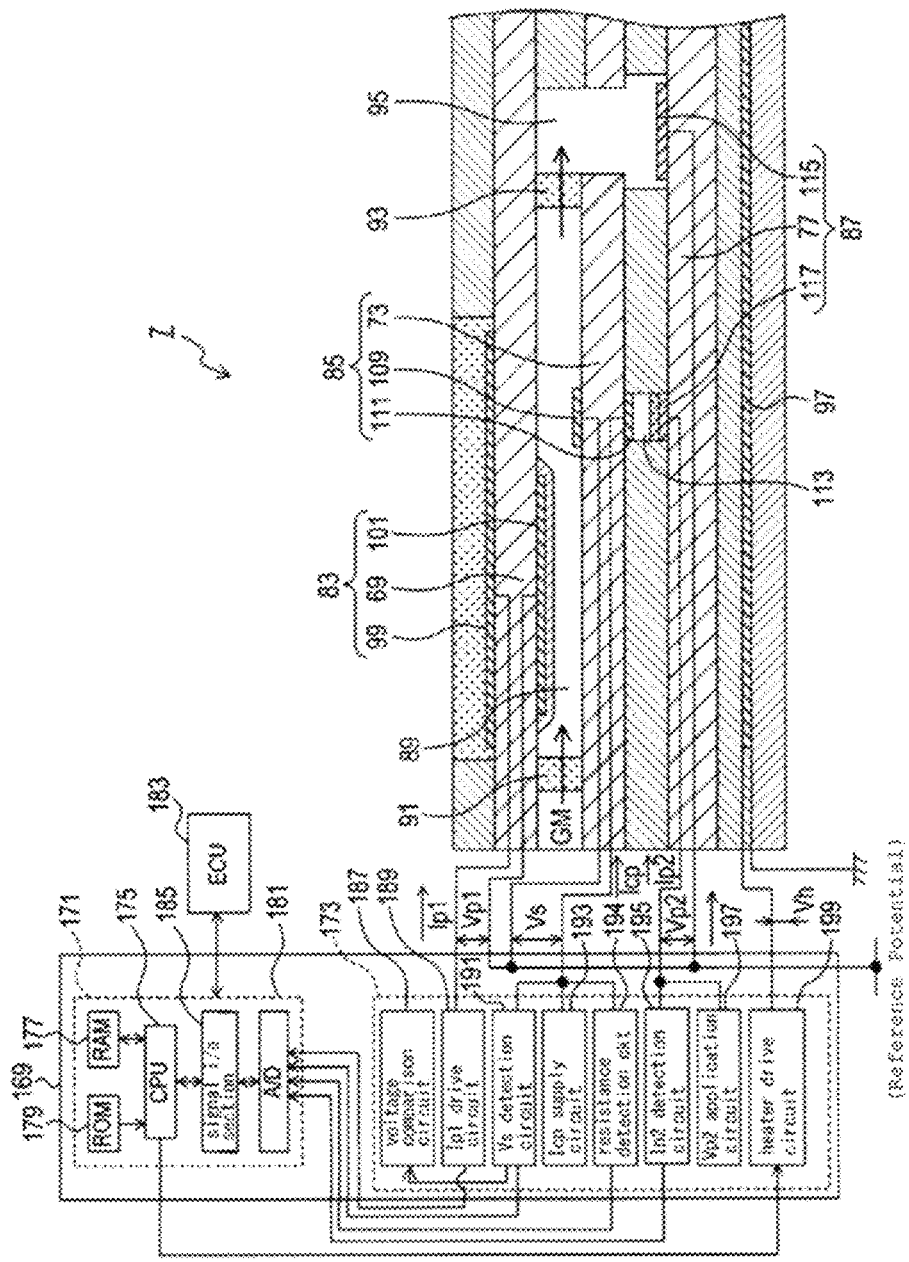
FIG. 6 is a diagram showing the configuration of a sensor control apparatus.

Next, the configuration of a sensor control apparatus 169 that controls operation of the sensor element 7 will be described with reference to FIG. 6. FIG. 6 is a diagram showing the configuration of the sensor control apparatus 169.

The sensor control apparatus 169 includes a microcomputer 171, an electric circuit section 173, etc. The microcomputer 171 includes a CPU 175 which executes various types of computations, a RAM 177 in which computation results, etc. are stored, and a ROM 179 which stores programs executed by the CPU 175, etc.

Also, the microcomputer 171 includes an A/D converter 181, a signal input/output section 185, an unillustrated timer clock, etc. The signal input/output section 185 is connected to the electric circuit section 173 via the A/D converter 181 and communicates with an ECU 183.

The electric circuit section 173 includes a reference voltage comparison circuit 187, an Ip1 drive circuit 189, a Vs detection circuit 191, an Icp supply circuit 193, a resistance detection circuit 194, an Ip2 detection circuit 195, a Vp2 application circuit 197, and a heater drive circuit 199. While being controlled by the microcomputer 171, the electric circuit section 173 detects the NOx concentration in the exhaust gas GM using the sensor element 7.

The first electrode 101, the third electrode 109, and the fifth electrode 115 are connected to a line maintained at a reference potential. One electrode of the heating resistor element 97 is grounded.

Next, a process for detecting the NOx concentration in the exhaust gas GM, which is executed by the sensor control apparatus 169 and the NOx sensor 1, will be described. The heater drive circuit 199 supplies drive current to the heating resistor element 97. The heating resistor element 97 heats the first to third solid electrolyte bodies 69, 73, and 77 so as to activate them. As a result, the first pump cell 83, the reference cell 85, and the second pump cell 87 start their respective operations.

The exhaust gas GM is introduced into the first measurement chamber 89, while the flow amount is limited by the first diffusion resistor section 91. The Icp supply circuit 193 supplies a weak current Icp which flows from the fourth electrode 111 to the third electrode 109 in the reference cell 85. Therefore, oxygen in the exhaust gas GM can receive electrons from the third electrode (negative electrode) 109 within the first measurement chamber 89. As a result, oxygen ions originating from the oxygen flow through the second solid electrolyte body 73 and move into the reference oxygen chamber 113. Namely, as a result of the current Icp flowing between the third electrode 109 and the fourth electrode 111, oxygen within the first measurement chamber 89 is fed into the reference oxygen chamber 113.

The Vs detection circuit 191 detects voltage Vs between the third electrode 109 and the fourth electrode 111. The voltage Vs corresponds to the difference between the oxygen concentration within the first measurement chamber 89 and the oxygen concentration within the reference oxygen chamber 113. The Vs detection circuit 191 compares the detected voltage Vs with a reference voltage (425 mV) using the reference voltage comparison circuit 187, and outputs the comparison result to the Ip1 drive circuit 189. When the oxygen concentration within the first measurement chamber 89 is adjusted such that the voltage Vs becomes constant in the vicinity of 425 mV, the oxygen concentration in the exhaust gas GM within the first measurement chamber 89 approaches a predetermine value (for example, $10^{-7}$ to $10^{-9}$ atm, preferably $10^{-8}$ atm).

In the case where the oxygen concentration of the exhaust gas GM introduced into the first measurement chamber 89 is lower than a predetermined value, the Ip1 drive circuit 189 causes the current Ip1 to flow through the first pump cell 83 such that the second electrode 99 serves as a negative electrode. As a result, the first pump cell 83 pumps oxygen from outside the sensor element 7 into the first measurement chamber 89. Meanwhile, in the case where the oxygen concentration of the exhaust gas GM introduced into the first measurement chamber 89 is higher than the predetermined value, the Ip1 drive circuit 189 causes the current Ip1 to flow through the first pump cell 83 such that the first electrode 101 serves as a negative electrode. As a result, the first pump cell 83 pumps oxygen out of the first measurement chamber 89 to outside the sensor element 7.

The exhaust gas GM whose oxygen concentration has been adjusted in the first measurement chamber 89 is introduced into the second measurement chamber 95 through the second diffusion resistor section 93. NOx in the exhaust gas GM having come into contact with the fifth electrode 115 within the second measurement chamber 95 is decomposed to $N_2$ and $O_2$ on the fifth electrode 115 as a result of applying a voltage Vp2 between the sixth electrode 117 and the fifth electrode 115 by the Vp2 application circuit 197. Oxygen produced as a result of the decomposition become oxygen ions, which flow through the third solid electrolyte body 77 and move into the reference oxygen chamber 113. Therefore, the current flowing through the second pump cell 87 assumes a value corresponding to the NOx concentration.

The sensor control apparatus 169 detects the current Ip2 flowing through the second pump cell 87 using the Ip2 detection circuit 195, and detects the NOx concentration in the exhaust gas GM from the current Ip2. Specifically, the relation between the NOx concentration and the current Ip2 is obtained beforehand, and, for example, a map representing the relation is made beforehand. The NOx concentration is obtained by applying the measured current Ip2 to the map.

For example, the NOx sensor 1 can be manufactured as follows.

First, ceramic sheets used as raw materials of the insulating layer 67, the first solid electrolyte body 69, the second solid electrolyte body 73, the third solid electrolyte body 77, and the insulating layers 79 and 81 are prepared. Through holes, etc. are appropriately formed in the ceramic sheets. Also, the insulating layers 71 and 75 are formed on the ceramic sheets by screen printing.

Next, in order to form the electrodes 99, 101, 109, 111, 115, and 117, pastes containing the materials of the electrodes are applied to the surfaces of corresponding ceramic sheets. The paste for forming the first electrode 101 contains platinum and $ZrO_2$. The paste for forming the remaining electrodes contains platinum as a main component.

Next, the ceramic sheets are stacked so as to form a laminate, and the laminate is fired. At that time, a first electrode precursor is formed in a region where the first electrode 101 is to be formed. The first electrode precursor contains platinum and $ZrO_2$. When the mass of platinum contained in the first electrode precursor is taken as 100 parts by mass, the mass of $ZrO_2$ contained in the first electrode precursor is 22 parts by mass. Also, the volume percentage of platinum in the first electrode precursor is 56 vol %, and the volume percentage of $ZrO_2$ in the first electrode precursor is 44 vol %.

Next, an aging treatment is performed for the first electrode precursor. The conditions of the aging treatment are described above. The temperature of the first electrode precursor is measured using an infrared radiation thermometer produced by CHINO Corporation.

As a result of the aging treatment, the first electrode precursor becomes the first electrode 101, whereby the gas sensor element 7 is completed.

Portions of the NOx sensor 1 other than gas sensor element 7 can be manufactured by known methods.

The present invention is not limited to the above-described embodiment, and can be practiced in various forms without departing from the scope of the present invention.

For example, the entirety or part of the portion of the first solid electrolyte body 69 not sandwiched between the first electrode 101 and the second electrode 99 may be formed of a material other than a solid electrolyte. Examples of the material other than a solid electrolyte include alumina, etc.

Similarly, the entirety or part of the portion of the second solid electrolyte body 73 not sandwiched between the third electrode 109 and the fourth electrode 111 may be formed of a material other than a solid electrolyte. Examples of the material other than solid electrolyte include alumina, etc.

The sensor of the present disclosure may be a sensor other than an NOx sensor. For example, the sensor of the present disclosure may be a sensor obtained by removing the second pump cell 87 from the above-described NOx sensor 1. This sensor can measure the oxygen concentration in the gas under measurement based on the amount of the current Ip1.

The ceramic component contained in the first solid electrolyte body 69 and the first electrode 101 may be other than zirconia. Examples of the ceramic component other than zirconia include $CeO_2$ (ceria), $ThO_2$ (thoria), $HfO_2$, $Bi_2O_3$, etc.

In the case where the ceramic component is $CeO_2$, as result of the aging treatment, coexistence regions containing $CeO_2$ are formed in the first electrode 101. In the case where the ceramic component is $ThO_2$, $HfO_2$, or $Bi_2O_3$, similarly, coexistence regions containing $ThO_2$, $HfO_2$, or $Bi_2O_3$ are formed.

The function of a single component in the above-described embodiments may be allotted to a plurality of components, or the functions of a plurality of components may be realized by a single component. Part of the configuration of each of the above-described embodiments may be omitted. At least part of the configuration of each of the above-described embodiments may be added to the configuration of another embodiment or may replace the configuration of another embodiment.

The present disclosure can be embodied not only in the form of the above-described NOx sensor, but also in other forms such as a system including the NOx sensor as a constituent element.

EXAMPLES

Example 1

An NOx sensor 1 was manufactured by the above-described method.

The temperature condition of the aging treatment was set as follows.

The atmosphere of the first electrode precursor: rich atmosphere

The temperature of the first electrode precursor: 800° C. to 870° C.

The temperature of the first electrode precursor was measured using an infrared radiation thermometer produced by CHINO Corporation.

The aging treatment conditions other than the temperature condition are as follows.

The atmosphere of the first electrode precursor in the aging treatment: $H_2$=2.35 vol %, $H_2O$=0.8 vol %, $N_2$=balance The voltage applied between the first electrode precursor and the second electrode 99 in the aging treatment: 0.77 V The time of the aging treatment: 40 sec After the aging treatment, the coexistence region area ratio SR of the first electrode 101 of the NOx sensor 1 was measured by the above-described method.

As a result, the coexistence region area ratio SR of the first electrode 101 was determined to be about 16% from the cross-sectional image shown in FIG. 4.

Example 2

A plurality of samples of the NOx sensor 1 were manufactured by the above-described method so that the samples differed in the coexistence region area ratio SR. For each sample of the NOx sensor 1, while the temperature of the sensor element 100 was changed by changing the temperature setting of the sensor control apparatus 169, the voltage Vp1 when the atmosphere was supplied as the gas under measurement was measured.

Figure 7:
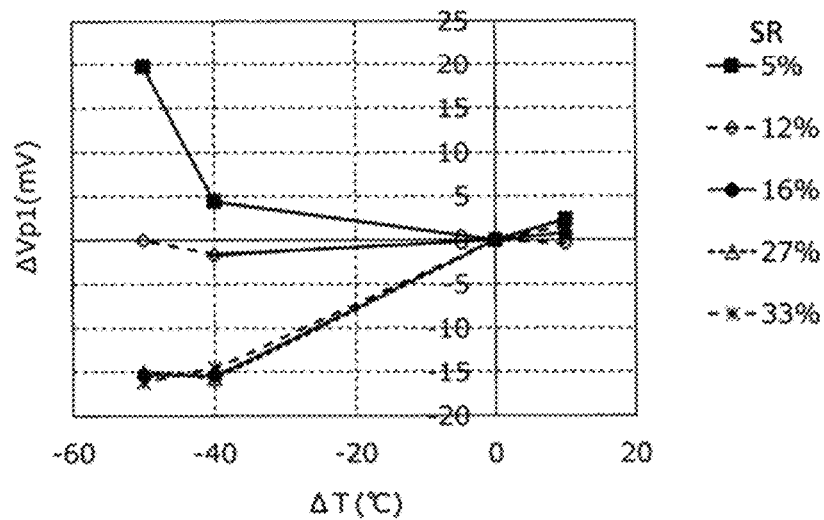
FIG. 7 is a graph showing the relation between sensor element temperature and Vp1 when the area ratio of coexistence regions is changed.

FIG. 7 shows the relation between the temperature of the sensor element 100 and the voltage Vp1 for the different coexistence region area ratios SR.

The horizontal axis of FIG. 7 shows changes ΔT in the temperature of the sensor element 100 in the case where a predetermined temperature TM is used as a reference (0). For example, "−40° C." means that the temperature of the sensor element 100 is 40° C. lower than the predetermined temperature TM. The vertical axis of FIG. 7 shows changes ΔVp1 in the voltage Vp1 in the case where the voltage Vp1 measured when the sensor element 100 having a coexistence region area ratio SR of 16% is maintained at the predetermined temperature TM is used as a reference (V0). For example, "5 mV" means that the voltage Vp1 of the sensor element 100 is 5 mV higher than the reference V0.

As shown in FIG. 7, in the case where the coexistence region area ratio SR was 16%, 27%, or 33%, the voltage Vp1 decreased as the temperature of the sensor element 100 decreased. This phenomenon occurred because the diffusion rate of the gas under measurement (atmosphere) decreases with an increase in temperature, and this represents a tendency that a normal sensor element exhibits.

Meanwhile, in the case where the coexistence region area ratio SR was 12% or 5%, even when the temperature of the sensor element 100 decreased, the voltage Vp1 hardly decreased (SR=12%) or rather increased (SR=5%). Conceivably, this phenomenon occurred because of the following reason. In the case where the coexistence region area ratio SR is 12% or 5%, when the temperature decreases due to the influence of a disturbance or the like, the internal resistance of the first electrode 101 increases and the voltage (Vp1) of the first pump cell 83 increases. This causes decomposition of a particular gas in the gas under measurement, which is a component to be measured, thereby lowering the measurement accuracy.

Also, in the case where the coexistence region area ratio SR is 16%, 27%, or 33%, while the influence of the diffusion rate of the gas under measurement on the temperature dependency of the voltage Vp1 is large, the influence of the coexistence region area ratio SR on the temperature dependency of the voltage Vp1 is small. Therefore, the measurement accuracy can be increased easily by design and/or correction in consideration of the temperature dependency of the voltage Vp1. However, in the case where the coexistence region area ratio SR is 12% or 5%, the influence of a factor, such as the internal resistance, which changes greatly with the value of the area ratio SR, on the temperature dependency of the voltage Vp1 increases. Therefore, it becomes difficult to increase the measurement accuracy by design or correction.

Example 3

A plurality of samples of the NOx sensor 1 were manufactured by the above-described method so that the samples differed in the coexistence region area ratio SR. For each sample of the NOx sensor 1, the temperature of the sensor element 100 was controlled to a predetermined temperature, the atmosphere was supplied as the gas under measurement, and the current Ip1 was measured in a predetermined period of time.

Figure 8:
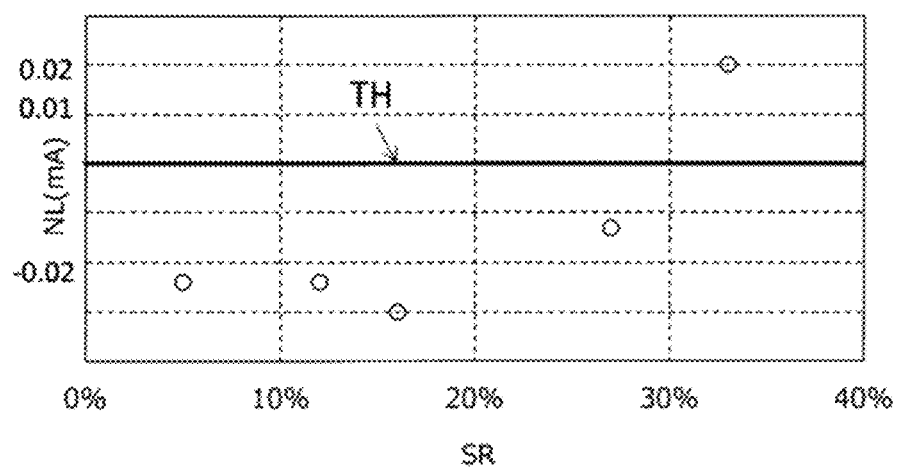
FIG. 8 is a graph showing Ip1 (specifically, noise level) when the area ratio of coexistence regions is changed.

FIG. 8 shows the current Ip1 (to be more exact, the noise level NL described below) when the coexistence region area ratio SR was changed.

The vertical axis of FIG. 8 shows the noise level NL which is the difference between the maximum and minimum values of the current Ip1 in the predetermined period of time. A thick line extending along the horizontal axis shows an allowable threshold TH of the noise level NL (when the noise level NL exceeds the threshold TH, the accuracy in measuring oxygen decreases). For example, "0.01 mA" represents that the noise level NL of the sensor element 100 is 0.01 mA higher than the threshold TH.

As shown in FIG. 8, when the coexistence region area ratio SR was 33%, the noise level NL increased sharply and exceeded the allowable threshold TH. In the case where the variation (noise) of the current Ip1 is large as described above, oscillation due to disturbing factors (for example, an abrupt change in the oxygen concentration in the gas under measurement or the gas flow velocity) becomes more likely to occur. Namely, it is considered that the difference in response between the third electrode 109 and the first electrode 101 containing the coexistence regions 207 increases, such that oscillation occurs easily.

It is understood from the above that when the area ratio SR is not less than 15.5% and is less than 30%, a decrease in measurement accuracy can be prevented, and oscillation can be prevented.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application claims priority from Japanese Patent Application No. 2019-171199 filed Sep. 20, 2019, and from Japanese Patent Application No. 2020-125870 filed Jul. 23, 2020, the above-noted applications incorporated herein by reference in their entirety.

What is claimed is:

1. A sensor element comprising:
    a measurement chamber;
    a pump cell for pumping out oxygen contained in a gas under measurement introduced into the measurement chamber and pumping oxygen into the measurement chamber, thereby adjusting oxygen concentration within the measurement chamber, the pump cell including a solid electrolyte body, an inner electrode formed on a surface of the solid electrolyte body that is exposed inside the measurement chamber, and an outer electrode formed on a surface of the solid electrolyte body that is located outside the measurement chamber; and
    a reference cell for generating a voltage corresponding to the oxygen concentration in the gas under measurement within the measurement chamber,
    wherein at least one electrode of the inner electrode and the outer electrode contains a noble metal and a component of the solid electrolyte body, and, when a cross section of the at least one electrode taken along a thickness direction thereof is observed, the at least one electrode has a plurality of noble metal regions formed of the noble metal, a plurality of solid electrolyte body regions formed of the component of the solid electrolyte body, a plurality of coexistence regions in which the noble metal and the component of the solid electrolyte body coexist, and a plurality of pores,
    wherein, in the entire cross section of the at least one electrode, an area ratio SR of the coexistence regions represented by following Equation I is not less than 15.5% and is less than 30%:

an area of the coexistence regions/(an area of the noble metal regions+an area of the solid electrolyte body regions+the area of the coexistence regions),  Equation I:

wherein the area ratio SR is determined using a Scanning Transmission Electron Microscopy/Energy Dispersive X-ray Spectroscopy (STEM/EDS) and a field emission scanning electron microscope (FE-SEM) image,
    wherein through the EDS analysis" to "wherein through EDS analysis, an area A of regions containing the noble metal, an area B of regions containing the component of the solid electrolyte body, and an area of regions where oxygen (O) is not detected are obtained,
    and through the FE-SEM, an area C of the entire cross section excluding the pores is obtained,
    then, the area of the coexistence regions is calculated as: the area A+the area B−the area C−the area of regions where O is not detected,
    finally, the area ratio SR is determined substitute the area of the coexistence regions into the Equation I which the area of the noble metal regions and the area of the solid electrolyte body regions are obtained using the FE-SEM.

2. The sensor element as claimed in claim 1, wherein the at least one electrode includes at least the inner electrode, and
    wherein the area ratio SR of the coexistence regions in the cross section of the inner electrode is not less than 15.5% and is less than 30%.

3. The sensor element as claimed in claim 1, wherein the area ratio SR of the coexistence regions is not less than 16% and is not greater than 27%.

4. The sensor element as claimed in claim 1, further comprising an NOx detection cell for measuring a concentration of nitrogen oxide in the gas under measurement having an adjusted oxygen concentration.

5. A gas sensor, comprising:
    the sensor element as claimed in claim 1, and
    a metallic shell which holds the sensor element.

6. A gas sensor unit comprising:
    the gas sensor as claimed in claim 5; and
    a gas sensor control section that is connected to the gas sensor,
    wherein the gas sensor control section is configured to feedback-control current flowing through the pump cell such that the reference cell has a constant potential.

* * * * *